(12) United States Patent
Guevremont et al.

(10) Patent No.: US 7,217,921 B2
(45) Date of Patent: May 15, 2007

(54) METHOD AND APPARATUS FOR FAIMS FOR IN-LINE ANALYSIS OF MULTIPLE SAMPLES

(75) Inventors: Roger Guevremont, Ottawa (CA); Ragnar Dworschak, Ottawa (CA)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 11/040,303

(22) Filed: Jan. 21, 2005

(65) Prior Publication Data

US 2005/0161598 A1     Jul. 28, 2005

Related U.S. Application Data

(60) Provisional application No. 60/537,881, filed on Jan. 22, 2004.

(51) Int. Cl.
    *H01J 49/40* (2006.01)
(52) U.S. Cl. .................. 250/287; 250/288; 250/281; 250/282
(58) Field of Classification Search ................ 250/281, 250/282, 287, 288
    See application file for complete search history.

(56) References Cited

U.S. PATENT DOCUMENTS 5,420,424 A     5/1995   Carnahan et al.
6,495,823 B1   12/2002   Miller et al.
6,504,149 B2    1/2003   Guevremont et al.
6,621,077 B1    9/2003   Guevremont et al.
6,653,627 B2 * 11/2003   Guevremont et al. ....... 250/288
6,690,004 B2    2/2004   Miller et al.
6,753,522 B2    6/2004   Guevremont et al.
6,787,765 B2    9/2004   Guevremont et al.
2004/0232326 A1 11/2004   Guevremont et al.

* cited by examiner

*Primary Examiner*—John R. Lee
*Assistant Examiner*—Jennifer Yantomo
(74) *Attorney, Agent, or Firm*—Freedman & Associates

(57) ABSTRACT

A method of separating ions includes providing a FAIMS analyzer region including an ion inlet orifice for providing ions thereto, and providing a sample holder along a side of the ion inlet orifice that is opposite the FAIMS analyzer. A sample material is applied to the sample holder such that sample material is disposed about first and second points along the sample holder, a distance between the first and second points being greater than a maximum dimension of the ion inlet orifice. The first point is aligned with the ion inlet orifice, and the sample material disposed about the first point is irradiated with laser light of a predetermined wavelength. Next, the sample holder is moved relative to the ion inlet so as to align the second point with the ion inlet orifice, and the sample material disposed about the second point is irradiated with laser light of a predetermined wavelength.

25 Claims, 7 Drawing Sheets

METHOD AND APPARATUS FOR FAIMS FOR IN-LINE ANALYSIS OF MULTIPLE SAMPLES

This application claims benefit from U.S. Provisional Application No. 60/537,881 filed Jan. 22, 2004.

FIELD OF THE INVENTION

The instant invention relates generally to High-Field Asymmetric Waveform Ion Mobility Spectrometry (FAIMS), and more particularly to FAIMS for in-line analysis of multiple samples.

BACKGROUND OF THE INVENTION

Biochemical and pharmaceutical applications have requirements for rapid screening and detection of compounds in extremely complex mixtures. Advances in chemical analysis technology applied to these fields must achieve a high degree of specificity in separations and incorporate systems that avoid slow separations, especially those involving chromatography and electrophoresis.

At present, the compounds in complex mixtures are separated and analyzed by chromatographic and electrophoretic methods combined with atmospheric pressure ionization-mass spectrometry (API-MS). In these separation techniques, a portion of a sample is introduced as a discrete pulse into the sample inlet of the API-MS system. The sample components are separated either through a component-specific interaction with mobile or stationary phases, or by differences in the drift velocities of components under the influence of electric fields. Because of the time that it takes for the components to migrate, chromatographic and electrophoretic methods require relatively long time periods to accomplish the separation, on the order of several minutes, whereas analysis by mass spectrometric methods provides data almost immediately. In practice, therefore, the mass spectrometer spends significant periods of time waiting for the arrival of transient signals. This is inefficient since the separation technology is very much less expensive than the MS instrumentation.

The above-mentioned problem is reduced when the separation technology operates in a continuous mode, for example the mixture is continuously delivered to the inlet of the separator and the selection of the separated components is electronically controlled. In this manner the MS acquires measurements of selected components in the mixture at almost full efficiency. Optionally, the MS is used to continuously study a particular component in a mixture until sufficient information is acquired. As will be obvious to one of ordinary skill in the art, operation of the separation technology in a continuous mode is impossible using existing chromatographic and electrophoretic techniques because the component of interest arrives only as a transient at the end of the separation. This transient mode of operation limits significantly the number and types of experiments that can be conducted during the lifetime of a given transient signal. Furthermore, if the information that is acquired during the transient is insufficient, a new sample must be injected and a delay is encountered during which the components are being separated.

Alternatively, complex mixtures may be studied using tandem mass spectrometry (MS/MS). With this technology, the ions are selected by a first mass analyzer operating at low pressure (e.g., $1\times10^{-5}$ torr) inside the vacuum chamber of a mass spectrometer, and are directed to enter a gas cell which is held at a higher bath gas pressure (e.g., $1\times10^{-3}$ torr). Upon entering this chamber, the ions collide with the molecules of bath gas and, if the kinetic energy of the ion is sufficient, the ion dissociates into some compound-specific fragments. The fragments pass out of the higher-pressure gas cell and are analyzed using a second mass analyzer, operating at a lower pressure, similar to that of the first mass analyzer. The advantage of tandem mass spectrometry is that the specificity is exceedingly high because of compound-specific fragmentation patterns that are created during the collision-induced dissociation. However, tandem MS requires considerable method development time and the operator must have expertise to operate the instrument. Furthermore, tandem MS cannot effectively quantify many kinds of isomeric ions (e.g., leucine and isoleucine) when both components coexist in the mixture. Accordingly, tandem MS is most suited to applications based on target compound analysis, where the system is used to search for a series of expected compounds and the identity of the expected fragment ions is known. Under these conditions the MS/MS experiment is capable of detecting ions at exceedingly low abundance, even in the presence of interfering compounds, since the MS/MS spectrum is very compound-specific. Tandem MS is less effective when used to study mixtures containing unknown components at trace concentrations. Since the existence of these unknowns cannot be predicted, the mass spectrum of the mixture must have peaks which are discernible above the background noise. In particular, detection of low intensity ions can be a problem when using the electrospray ionization (ESI) technique, since ESI produces background ions that elevate the baseline intensity along the mass-to-charge ratio axis of a mass spectrum. This background of ions makes detection of unknown trace components difficult, if not impossible.

Of course, complex mixtures may also be analyzed using mass spectrometers with extremely high resolution, such as FT-ICR systems. However, high resolution mass spectrometers are very expensive.

FAIMS is a relatively new separation technique, which solves a number of the problems that are associated with the above-mentioned prior art techniques. FAIMS separates ions on a continuous basis, with the separation occurring under electronic control. Additionally, FAIMS reduces the background chemical noise inherent to atmospheric pressure ionization techniques, thus reducing the detection limits for unknown components in complex mixtures. Finally, FAIMS optionally is operated in tandem with many of the other technologies that are noted above, because the FAIMS device is located between the ion source and the mass spectrometer. A consequence of this physical location is that the FAIMS apparatus can be operated in conjunction with chromatography, electrophoresis, tandem mass spectrometry and high resolution mass spectrometry, etc.

Typically, ions are introduced into a FAIMS device after being formed by atmospheric pressure ionization, such as for instance corona discharge ionization, ionization by radioactive Ni, and electrospray ionization as just a few non-limiting examples. In each of these cases, the sample is one of a liquid and a gas, and in every case the analyte ions are suspended in a gas. One notable exception is found in U.S. Pat. No. 6,653,627, issued on Nov. 25, 2003 in the name of Guevremont et al., which discloses a FAIMS apparatus and method using a laser based ionization source. The entire contents of U.S. Pat. No. 6,653,627 are incorporated herein by reference. In that case, a matrix-supported sample is deposited on a target surface that is disposed within the FAIMS analyzer region, and irradiation is performed using a laser that is disposed external to the FAIMS analyzer region. Since ions are formed within the analyzer region, problems associated with low ion transmission efficiency through an ion inlet are eliminated. Unfortunately, in order to introduce new sample it is necessary to disassemble the FAIMS electrode assembly, remove the existing target surfaces, prepare new target surfaces, introduce the new target surfaces, and finally reassemble the FAIMS electrode assembly. Of course, this sample introduction technique does not support rapid screening of samples, and is very time consuming.

Placing the target surface of the laser source at a location that is external to the FAIMS analyzer reduces the time and labor that is required for introducing new samples into the FAIMS. In order to achieve high ion transmission efficiency into the FAIMS analyzer region, the target surface should be located as close as possible to the ion inlet orifice of the FAIMS, and should also be disposed parallel to the ion inlet orifice. Unfortunately, when the target surface is disposed for achieving high ion transmission efficiency, very little space remains for arranging the laser light source at a position for irradiating the target surface.

It would be advantageous to provide a method and an apparatus for introducing ions, that are formed using a laser source, through an inlet into a FAIMS analyzer region, with high ion transmission efficiency. It would be further advantageous to provide a method and an apparatus for introducing such ions in a manner that supports rapid screening and in-line analysis of samples.

SUMMARY OF THE INVENTION

It is an object of at least some of the embodiments of the instant invention to provide a method and an apparatus that overcomes at least some of the above-mentioned limitations of the prior art.

It is also an object of at least some of the embodiments of the instant invention to provide a method and an apparatus for introducing into the analyzer region of FAIMS, analyte ions from solid samples or from samples containing large biological and polyatomic molecules.

It is also an object of at least some of the embodiments of the instant invention to provide a method and an apparatus for introducing analyte ions from sample compounds, in a manner that supports rapid screening of samples.

According to a first aspect of the instant invention, provided is an apparatus for separating ions, comprising: a FAIMS analyzer comprising a first electrode and a second electrode that is spaced apart from the first electrode, a space between the first electrode and the second electrode defining an analyzer region; an ion inlet orifice defined within a portion of the first electrode, for providing fluid communication between the analyzer region and a region that is external to the analyzer region; and, a laser-based ionization source comprising a laser light source and a multiple sample holder, the multiple sample holder disposed within the region that is external to the analyzer region for supporting each of a plurality of discrete sample portions, during different non-overlapping periods of time, in an aligned relationship with the ion inlet orifice, wherein the laser light source is synchronized to irradiate, with light of a predetermined wavelength, each of the plurality of discrete sample portions when in the aligned relationship with the ion inlet orifice.

According to another aspect of the instant invention, provided is an apparatus for separating ions, comprising: a FAIMS analyzer comprising a first electrode and a second electrode that is spaced apart from the first electrode, a space between the first electrode and the second electrode defining an analyzer region; an ion inlet orifice comprising a finite-sized opening that is defined within a portion of the first electrode, the ion inlet orifice for providing fluid communication between the analyzer region and a region that is external to the analyzer region; and, a laser-based ionization source for producing ions from a sample material, the laser-based ionization source comprising: a sample holder disposed within the region that is external to the analyzer region, the sample holder having at least a target region for supporting a sample material, the at least a target region including a first portion and a second portion, the first portion and the second portion combined having a total surface area that is larger than the finite-sized opening of the ion inlet orifice; an actuator for moving the sample holder relative to the ion inlet orifice, so as to align the first portion of the at least a target region with the ion inlet orifice during a first period of time and to align the second portion of the at least a target region with the ion inlet orifice during a second period of time; and, a laser light source disposed to irradiate, with light of a predetermined wavelength, the first portion of the at least a target region during the first period of time and the second portion of the at least a target region during the second period of time.

According to yet another aspect of the instant invention, provided is a method of separating ions, comprising: providing a FAIMS analyzer region including an ion inlet orifice for providing ions thereto; providing a sample holder along a side of the ion inlet orifice that is opposite the FAIMS analyzer region; applying a sample material to the sample holder such that sample material is disposed about first and second points along the sample holder, a distance between the first and second points being greater than a maximum dimension of the ion inlet orifice; aligning the first point with the ion inlet orifice; irradiating the sample material disposed about the first point with laser light of a predetermined wavelength; moving the sample holder relative to the ion inlet so as to align the second point with the ion inlet orifice; and, irradiating the sample material disposed about the second point with laser light of a predetermined wavelength.

The entire contents of U.S. Provisional application 60/537,881 filed Jan. 22, 2004, are hereby incorporated by reference.

BRIEF DESCRIPTION OF THE DRAWINGS

Exemplary embodiments of the invention will now be described in conjunction with the following drawings, in which similar reference numerals designate similar items.

DESCRIPTION OF EMBODIMENTS OF THE INSTANT INVENTION

Figure 1:
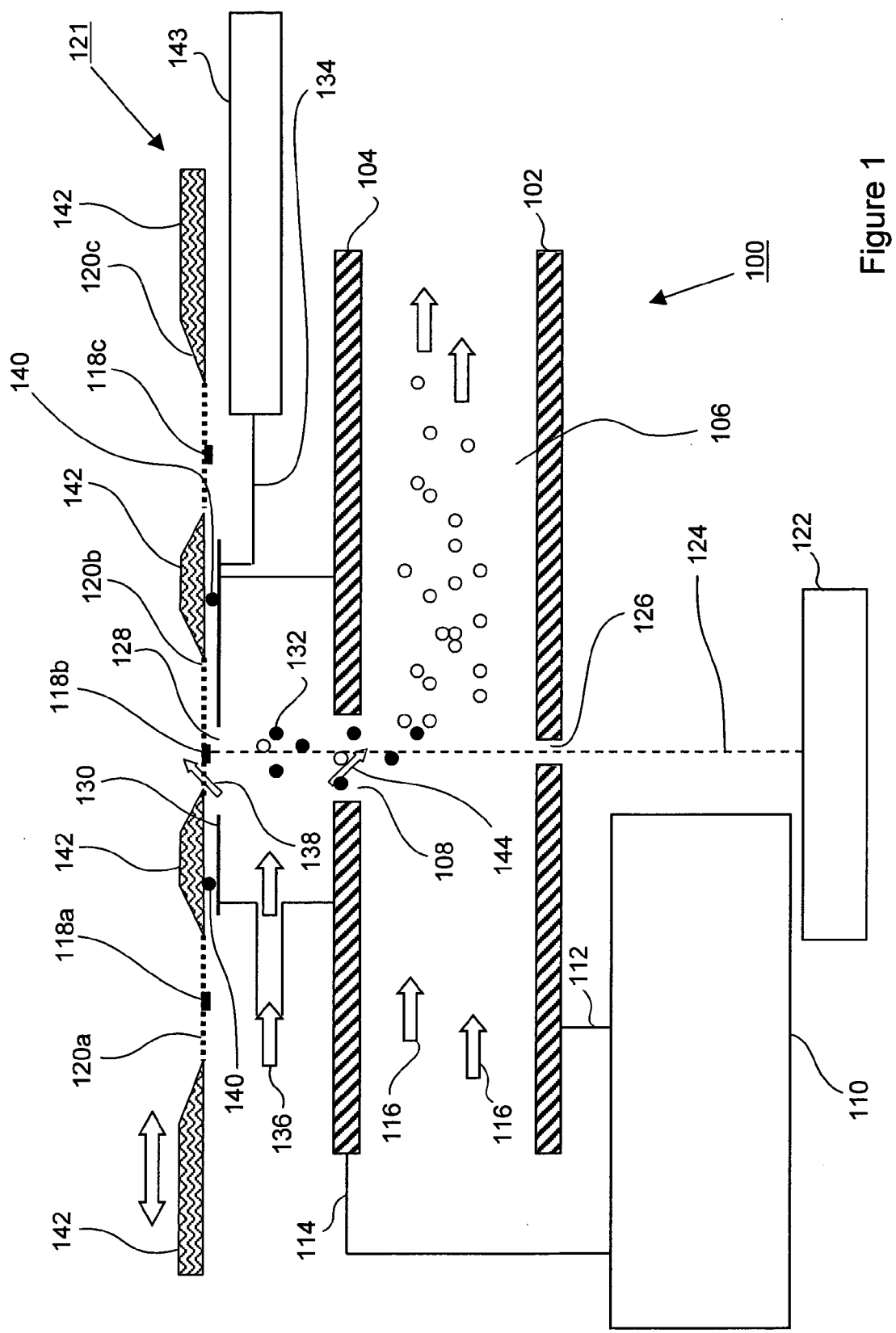
FIG. 1 is a simplified longitudinal cross sectional view of a system according to an embodiment of the instant invention, including a MALDI ion source with a multiple sample holder, and a FAIMS.

Exemplary embodiments of the invention will now be described in conjunction with the accompanying drawings. The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Throughout the detailed description, reference is made primarily to atmospheric pressure MALDI, although it is to be understood that other atmospheric pressure ionization techniques, particularly laser based techniques such as atmospheric pressure laser desorption chemical ionization (AP/LD/CI), are readily interfaced to FAIMS using the general concepts presented herein. Furthermore, for the following discussions it is inconvenient to list all the possible versions of atmospheric pressure laser desorption chemical ionization (AP/LD/CI), atmospheric pressure matrix assisted laser desorption/ionization (MALDI), and so on, that appear in the literature. Accordingly, the word MALDI is used as a representative example of one of many laser based ionization schemes that are appropriate for producing ions within the context of the embodiments of the instant invention. The laser optionally desorbs the molecule of interest from a surface, a matrix, or a polymer support as some non-limiting examples, and the laser beam may or may not be involved in the ionization process. Optionally, hybrid schemes that include more than one process are used to produce ions. For example, ions are produced by laser desorption with ionization using a second laser for multi-photon excitation. In another example, molecules of a sample are volatilized from a surface followed by gas-phase chemical ionization using a remotely produced reactant ion. These examples are presented merely to illustrate the nature of ionization methods appropriate for the inventions described below and are not intended to limit the scope of possible laser-based ionization methods that can be used in conjunction with the instant invention. The instant invention addresses the problem of combining a laser beam and sample holder and a mechanism for desolvating and delivering ions into a FAIMS for ion separation. Finally, although reference is made primarily to atmospheric pressure MALDI, it is understood that the pressure and temperature of the MALDI source and of FAIMS is optionally controllable, and that the operating conditions are selected to obtain a sensitivity and separation as required for the chemical analysis. The examples of operating pressures and temperatures in this application are taken for illustrations and should be considered as non-limiting examples.

Referring to FIG. 1, shown is a simplified longitudinal cross sectional view of a system according to an embodiment of the instant invention, including an atmospheric pressure MALDI ion source with a multiple sample holder, and a FAIMS. The FAIMS 100 includes a first FAIMS electrode 102 and a second FAIMS electrode 104. The first FAIMS electrode 102 and the second FAIMS electrode 104 are disposed in a spaced-apart facing arrangement and define a FAIMS analyzer region 106 therebetween. Ions enter the FAIMS analyzer region via an ion inlet orifice 108 that is defined within a portion of the second FAIMS electrode 104. A curtain gas region is provided adjacent to the ion inlet orifice 108, to assist in desolvation of ions and to direct neutral molecules away from the ion inlet orifice 108. Ions in FAIMS 100 are separated by application of an asymmetric waveform dispersion voltage (DV) and a direct current compensation voltage (CV) by power supply 110, which is in electrical communication with the first FAIMS electrode 102 via an electrical coupling 112 and with the second FAIMS electrode 104 via an electrical coupling 114. The voltages applied to the first FAIMS electrode 102 and the second FAIMS electrode 104 create electric fields between these electrodes that separate the ions while the ions are transported by a flow of carrier gas 116 along the analyzer region 106. In FIG. 1 the first FAIMS electrode 102 and the second FAIMS electrode 104 are shown as parallel conductive plates, but are optionally micromachined (MEMS) parallel non-curved or curved surfaces, or further optionally, are non-conductive materials that are coated with a conductive layer.

During use, a first sample spot 118a is applied to a first discrete target region 120a, a second sample spot 118b is applied to a second discrete target region 120b, etc. In the embodiment that is shown at FIG. 1, preferably each discrete target region 120a, 120b, etc. is fabricated from a material that is opaque, and therefore does not transmit, light at a wavelength of laser light provided from a laser source 122. Optionally, each discrete target region 120a, 120b, etc. is electrically conductive. Collectively, the discrete target regions 120a, 120b, etc. comprise a multiple sample holder 121. In the instant embodiment, the multiple sample holder 121 is a 1-row by n-column multiple sample strip.

A laser beam 124 is projected from the laser light source 122, along an optical path through a laser orifice 126 defined within the first FAIMS electrode 102, through a portion of the analyzer region 106 and outwardly through ion inlet orifice 108 and through a curtain gas orifice 128 defined within a curtain gas plate 130. During separate, non-overlapping periods of time, the laser beam 124 impinges upon the sample spots 118a, 118b, etc. and ionizes some of the compounds contained therein. Advantageously, by passing the laser beam 124 through curtain gas orifice 128 of curtain plate 130, the laser beam 124 strikes the sample spots 118a, 118*b*, etc. at an angle close to perpendicular to the corresponding discrete target region 120*a*, 120*b*, etc. An ion cloud 132 produced by the laser beam impinging upon, for instance, sample spot 118*b* is directed towards the curtain plate 130 of FAIMS 100 by application of voltages to the multiple sample holder 121 by a not illustrated power supply, and to the curtain plate 130 by power supply 143 via electrical coupling 134. A curtain gas flow 136 is provided in the space between the curtain plate 130 and the second FAIMS electrode 104. A portion 138 of the curtain gas flow 136 passes outwards through curtain gas orifice 128, and an analyzer gas portion 144 flows into the analyzer region 106 between the first FAIMS electrode 102 and the second FAIMS electrode 104, via the ion inlet orifice 108. The portion 138 serves to redirect away from the entrance to FAIMS 100 the neutral molecules that are generated by the laser beam 124 striking the sample spot 118*b*, for example, and prevents these neutral molecules from entering the space between the curtain plate 130 and the second FAIMS electrode 104. At the same time, the ions 132 are directed towards FAIMS 100 by electric fields generated by voltages applied to the multiple sample holder 121, the curtain plate 130 and the second FAIMS electrode 104. The analyzer gas flow 144 also assists in the transfer of ions into the FAIMS analyzer region 106. Preferably, the each discrete target region 120*a*, 120*b*, etc. is at least partly porous or permeable to a flow of a curtain gas 136, such that a portion 138 of the carrier gas 136 is transmitted through the discrete target region 120*a*, 120*b*, etc., and therefore carries away neutral molecules generated when a laser beam 124 originating at laser source 122 strikes the sample spot 118*a*, 118*b*, etc. For instance, each discrete target region 120*a*, 120*b*, etc. is fabricated from a fine metallic mesh or a fine metal screen that has the desired properties of transparency to the laser beam, electrical conductivity and porosity for passage of the flow 138 of a portion of a carrier gas 136.

Since each discrete target region 120*a*, 120*b*, etc. of the multiple sample holder 121 is moved into a parallel relationship adjacent to the curtain plate 130 prior to the sample spot 118*a*, 118*b* supported thereon being irradiated by the laser beam 124, the ions that are produced are directed in a straight-line trajectory from the discrete target region 120*a*, 120*b*, etc. towards the curtain plate 130. The ions pass through the curtain gas orifice 128 and are further directed towards ion inlet orifice 108 in the second FAIMS electrode 104 by the electric field between the curtain plate 130 and the second FAIMS electrode 104. Advantageously, the multiple sample holder 121 and the curtain plate 130 are sufficiently close together during use to maximize the likelihood of ions produced from the sample spots 118*a*, 118*b*, etc. entering the curtain gas orifice 128 of the curtain plate 130. Optionally, a seal 140 is provided for establishing a gas-tight fit between the curtain plate 130 and a solid support portion 142 of the multiple sample holder 121. The distance between the multiple sample holder 121 and the curtain plate 130 is established by optimization of the intensity of signals detected for the ions of interest.

Note also that it is necessary to prevent contamination from the laser orifice 126 from entering the gas flow in FAIMS. This is achieved optionally by providing a window across the laser orifice 126 through which the laser is directed, or by providing a flow of gas outward from the analyzer region 106 and through laser orifice 126 to carry away potential contaminants.

Figure 2:
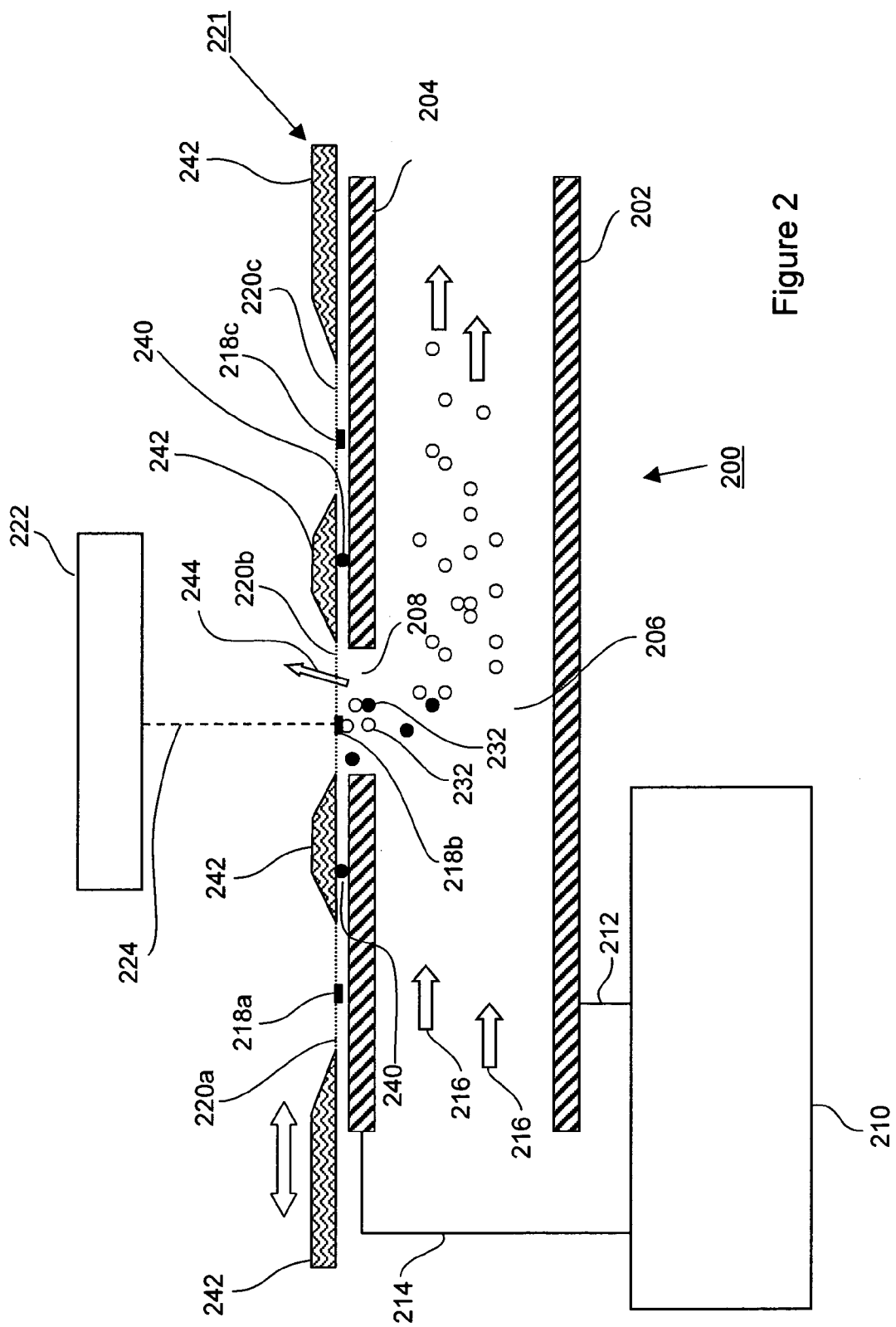
FIG. 2 is a simplified longitudinal cross sectional view of a system according to another embodiment of the instant invention, including an atmospheric pressure MALDI ion source with a multiple sample holder, and a FAIMS.

Referring now to FIG. 2, shown is a simplified longitudinal cross sectional view of a system according to another embodiment of the instant invention, including an atmospheric pressure MALDI ion source with a multiple sample holder, and a FAIMS. The system shown at FIG. 2 operates with a modified curtain gas approach for preventing neutrals from entering FAIMS 200. The FAIMS 200 includes a first FAIMS electrode 202 and a second FAIMS electrode 204. The first FAIMS electrode 202 and the second FAIMS electrode 204 are disposed in a spaced-apart facing arrangement and define a FAIMS analyzer region 206 therebetween. Ions enter the FAIMS analyzer region 206 via an ion inlet orifice 208 that is defined within a portion of the second FAIMS electrode 204. Ions in FAIMS 200 are separated by application of an asymmetric waveform dispersion voltage (DV) and a direct current compensation voltage (CV) by power supply 210, which is in electrical communication with the first FAIMS electrode 202 via an electrical coupling 212 and with the second FAIMS electrode 204 via an electrical coupling 214. The voltages applied to the first FAIMS electrode 202 and the second FAIMS electrode 204 create electric fields between these electrodes that separate the ions while the ions are transported by a flow of carrier gas 216 along the analyzer region 206 from the ion inlet orifice to a not illustrated ion outlet. In FIG. 2 the first FAIMS electrode 202 and the second FAIMS electrode 204 are shown as parallel conductive plates, but are optionally micromachined (MEMS) parallel non-curved or curved surfaces, or further optionally are non-conductive materials that are coated with a conductive layer.

During use, a first sample spot 218*a* is applied to a front surface of first discrete target region 220*a*, a second sample spot 218*b* is applied to a front surface of second discrete target region 220*b*, etc. In the embodiment that is shown at FIG. 2, each discrete target region 220*a*, 220*b*, etc. is fabricated from a material that is at least one of partially transmissive and partly transmissive to light at a wavelength of laser light provided from a laser source 222. Optionally, each discrete target region 220*a*, 220*b*, etc. is electrically conductive. Furthermore, the each discrete target region 220*a*, 220*b*, etc. is at least partly porous or permeable to a flow of a carrier gas 216, such that a portion 244 of the carrier gas 216 is transmitted through the discrete target region 220*a*, 220*b*, etc., and therefore carries away neutral molecules generated when a laser beam 224 originating at laser source 222 strikes the sample spot 218*a*, 218*b*, etc. For instance, each discrete target region 220*a*, 220*b*, etc. is fabricated from a fine metallic mesh or a fine metal screen that has the desired properties of transparency to the laser beam, electrical conductivity and porosity for passage of the flow 244 of a portion of a carrier gas 216 out through the ion inlet orifice 208.

Collectively, the discrete target regions 220*a*, 220*b*, etc. comprise a multiple sample holder 221. In the instant embodiment, the multiple sample holder 221 is a 1-row by n-column multiple sample strip.

During use, the laser beam 224 is directed to strike a back surface of each discrete target region 220*a*, 220*b*, etc., one at a time, while the sample spot 118*a*, 118*b*, etc. is supported at the front surface of the respective discrete target region and facing into the analyzer region 206 of FAIMS 200. A portion of the laser light is transmitted through the discrete target region 220*a*, 220*b*, etc. to the sample spot 218*a*, 218*b*, etc., and ionizes some of the compounds contained therein. Ions 232 that are produced by the laser beam 224 striking the sample spot, for instance sample spot 218*b* in FIG. 2, are directed into the FAIMS analyzer region 206. Advantageously, the ions 232 pass almost immediately into the FAIMS analyzer region 206 via ion inlet orifice 208 without traversing a separate curtain gas region that is external to the FAIMS analyzer region 206. Once inside the FAIMS analyzer region 206, those ions that do not posses stable trajectories under the influence of the applied CV and DV are lost rapidly to an electrode surface. Accordingly, the probability of an ion of interest recombining with another ion of opposite polarity is reduced. Furthermore, the neutral molecules generated when the laser beam 224 strikes the sample spot, for instance sample spot 118*b*, are prevented from entering the FAIMS analyzer region 206 by the flow of gas 244 outwards through the discrete target region 220*b*.

Since each discrete target region 220*a*, 220*b*, etc. of the multiple sample holder 221 is moved into a parallel relationship adjacent to the ion inlet orifice 208 of the second FAIMS electrode 204 prior to the sample spot 218*a*, 218*b* supported thereon being irradiated by the laser beam 224, the ions that are produced are directed in an efficient manner from the discrete target region 220*a*, 220*b*, etc. towards ion inlet orifice 208. Advantageously, the multiple sample holder 221 and the second FAIMS electrode 204 are sufficiently close together during use to maximize the percentage of ions produced from the sample spots 218*a*, 218*b*, etc. that enter the ion inlet orifice 208. Optionally, a seal 240 is provided for establishing a gas-tight fit between the second FAIMS electrode 204 and a solid support portion 242 of the multiple sample holder 221. The distance between the multiple sample holder 221 and the second FAIMS electrode 204 is established by optimization of the intensity of signals detected for the ions of interest.

In FIG. 2, the first FAIMS electrode 202 and the second FAIMS electrode 204 are shown as planar conductive electrodes. Optionally, electrodes according to other FAIMS electrode geometries are used, such as for instance micromachined (MEMS) parallel non-curved or curved surfaces. Further optionally, the electrodes are fabricated from non-conductive materials and are coated with a conductive outer layer. Many types of FAIMS geometry may optionally be used, including domed inner electrodes, side-to-side configurations, parallel plates, and spherical geometry, as some non-limiting examples.

Figure 3:
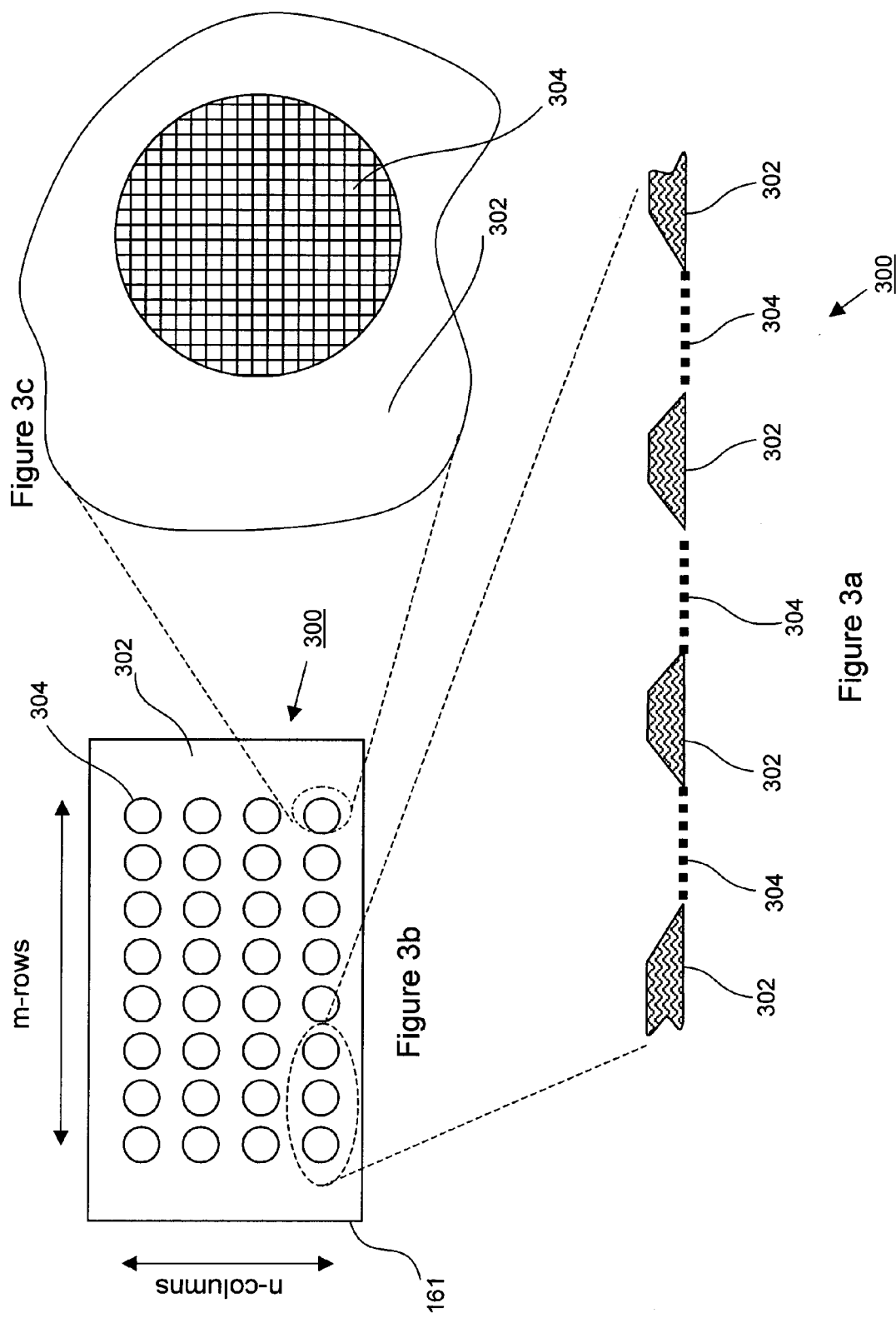
FIG. 3a is a partial longitudinal cross sectional view of a m-row by n-column multiple sample holder according to an embodiment of the instant invention.
FIG. 3b is a top view of a m-row by n-column multiple sample holder according to an embodiment of the instant invention.
FIG. 3c is an enlarged top view of one discrete target region of a m-row by n-column multiple sample holder according to an embodiment of the instant invention.

Referring now to FIG. 3*a*, shown is a partial longitudinal cross sectional view of a m-row by n-column multiple sample holder 300 according to an embodiment of the instant invention. FIG. 3*a* shows an edge-on view of the multiple sample holder 300, which illustrates that a solid support region 302 is optionally thick relative to discrete target regions 304. The dotted lines of discrete target regions 304 denote in FIG. 3*a* a mesh material. Preferably the discrete target regions 304 are formed of a thin metallic mesh or screen that is at least partly conductive in order to carry electric charges that are generated when a laser beam strikes a not illustrated sample spot supported on one of the discrete target regions 304. By conducting away electric charges, the mesh or screen does not accumulate sufficient electrostatic charge to create electric fields that adversely affect the formation or transport of ions produced by a pulse of laser radiation striking the sample spot. When mounted to a FAIMS system, in a manner similar to that shown in FIG. 1 or FIG. 2, the multiple sample holder 300 is translated to bring each of the discrete target regions 304 into juxtaposition with an ion inlet orifice of the FAIMS system. To this end, preferably an actuator (not shown) is provided for translating the multiple sample holder relative to the ion inlet, in order to make analytical measurements on each one of a plurality of samples, supported one sample on each discrete target region 304, in rapid succession or in-line with another separation technique. Optionally, the discrete target regions 304 are formed of a material that is also partly transparent to the wavelength of the laser radiation, for supporting irradiation of the sample spot by a laser beam that impinges on a back surface of the discrete target region, as shown for example at FIG. 2.

Referring now to FIG. 3*b*, shown is a top view of a m-row by n-column multiple sample holder according to an embodiment of the instant invention. The number of rows and the number of columns of discrete target regions 304 in the multiple sample holder 300 is not critical.

Referring now to FIG. 3*c*, shown is an enlarged top view of one discrete target region of a m-row by n-column multiple sample holder according to an embodiment of the instant invention. The discrete target region 304 is preferably formed of a thin metallic mesh or screen. During use, a spot of a sample is applied to a front surface of the discrete target region 304. Optionally, a spot of a sample is applied to a back surface of the discrete target region 304, and the sample material is carried through the mesh or screen material to the front side by capillary action.

Figure 4:
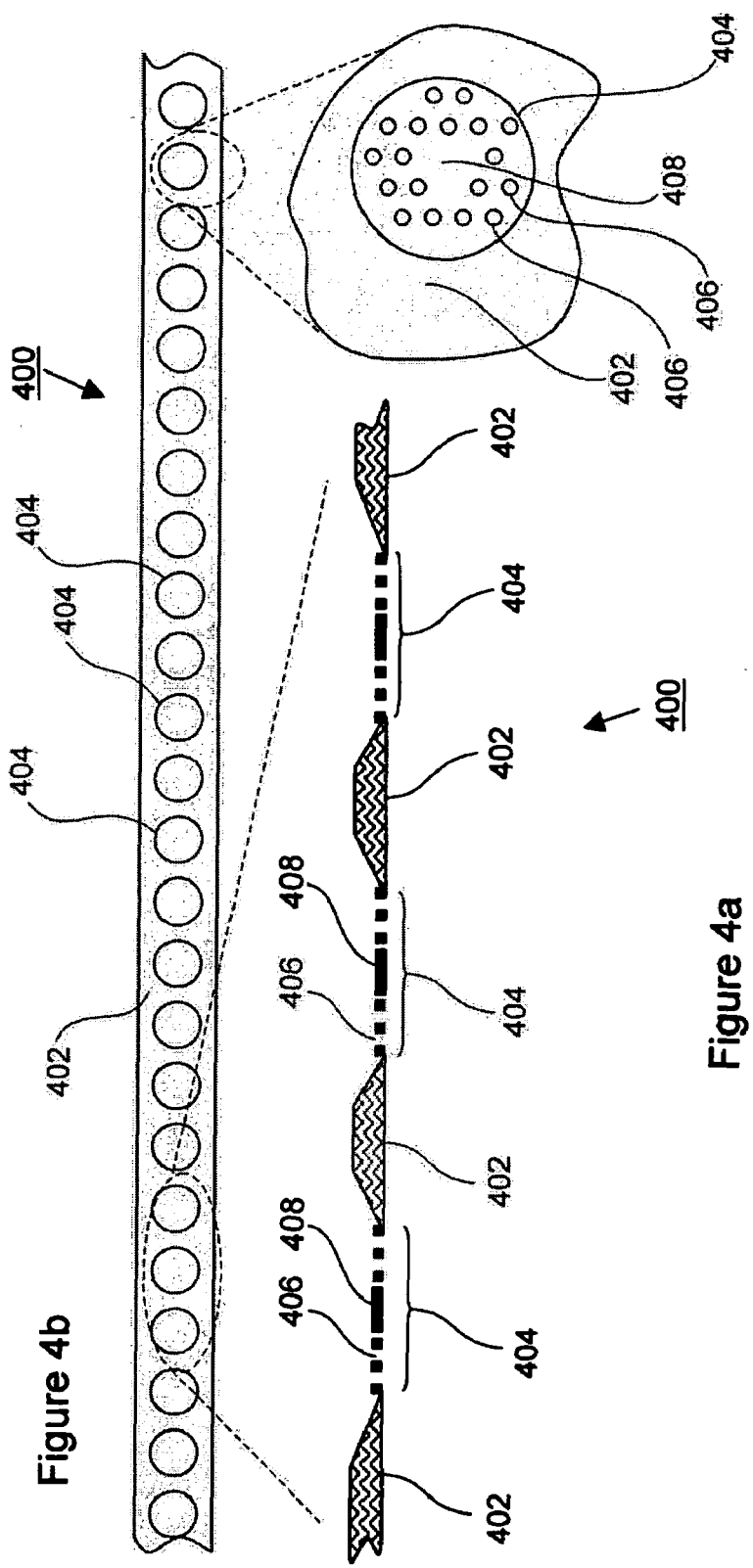
FIG. 4a is a partial longitudinal cross sectional view of a 1-row by n-column multiple sample holder according to an embodiment of the instant invention.
FIG. 4b is a top view of a 1-row by n-column multiple sample holder according to an embodiment of the instant invention.
FIG. 4c is an enlarged top view of one discrete target region of a 1-row by n-column multiple sample holder according to an embodiment of the instant invention.

Referring now to FIG. 4*a*, shown is a partial longitudinal cross sectional view of a 1-row by n-column multiple sample holder 400 according to an embodiment of the instant invention. According to this embodiment, the multiple sample holder 400 is formed into an elongated strip. FIG. 4*a* shows an edge-on view of the multiple sample holder 400, which illustrates that a solid support region 402 is optionally thick relative to discrete target regions 404. The dotted lines of discrete target regions 404 denote in FIG. 4*a* a mesh material. Preferably the discrete target regions 404 are formed of a thin metallic mesh or screen that is at least partly conductive in order to carry electric charges that are generated when a laser beam strikes a not illustrated sample spot supported on one of the discrete target regions 404. By carrying away electric charges, the mesh or screen does not accumulate sufficient electrostatic charge to create electric fields that adversely affect the formation or transport of ions produced by a pulse of laser radiation striking the sample spot. When mounted to a FAIMS system, in a manner similar to that shown in FIG. 1 or FIG. 2, the multiple sample holder 400 is translated to bring each of the discrete target regions 404 into juxtaposition with an ion inlet orifice of the FAIMS system. To this end, preferably an actuator (not shown) is provided for translating the multiple sample holder 400 relative to the ion inlet, in order to make analytical measurements on each one of a plurality of samples, supported one sample on each discrete target region 404, in rapid succession or in-line with another separation technique. Optionally, the discrete target regions 404 are formed of a material that is also partly transparent to the wavelength of the laser radiation, for supporting irradiation of the sample spot by a laser beam that impinges on a back surface of the discrete target region, as shown for example at FIG. 2.

Referring now to FIG. 4*b*, shown is a top view of a 1-row by n-column multiple sample strip according to an embodiment of the instant invention. The number of columns is not critical.

Referring now to FIG. 4*c*, shown is an enlarged top view of one discrete target region 404 of a 1-row by n-column multiple sample strip according to an embodiment of the instant invention. FIG. 4*c* shows additional optional features of the discrete target region 404. In particular, the discrete target region 404 is fabricated optionally from a thin material, preferably a metallic foil, which includes a non-perforated sample deposition region 408 that is surrounded by a region of gas transport holes 406. Each sample is sprayed, or otherwise deposited, on one of the sample deposition regions 408. During automatic multiple sample operation, a not illustrated actuator brings each sample deposition region 408 of a discrete target region 404 into the optical path of a laser beam of a not illustrated MALDI laser. The neutral molecules of sample and matrix (if used) are carried in a direction away from FAIMS by the gas flowing outwards through the gas transport holes 406. In this case, the sample is deposited on a side of the sample deposition region 408 that faces towards the ion inlet orifice of FAIMS. Optionally, the discrete target regions 404 are formed of a material that is also partly transparent to the wavelength of the laser radiation, for supporting irradiation of the sample spot by a laser beam that impinges on a back surface of the sample deposition region 408 of the discrete target region, as shown for example at FIG. 2.

Figure 5:
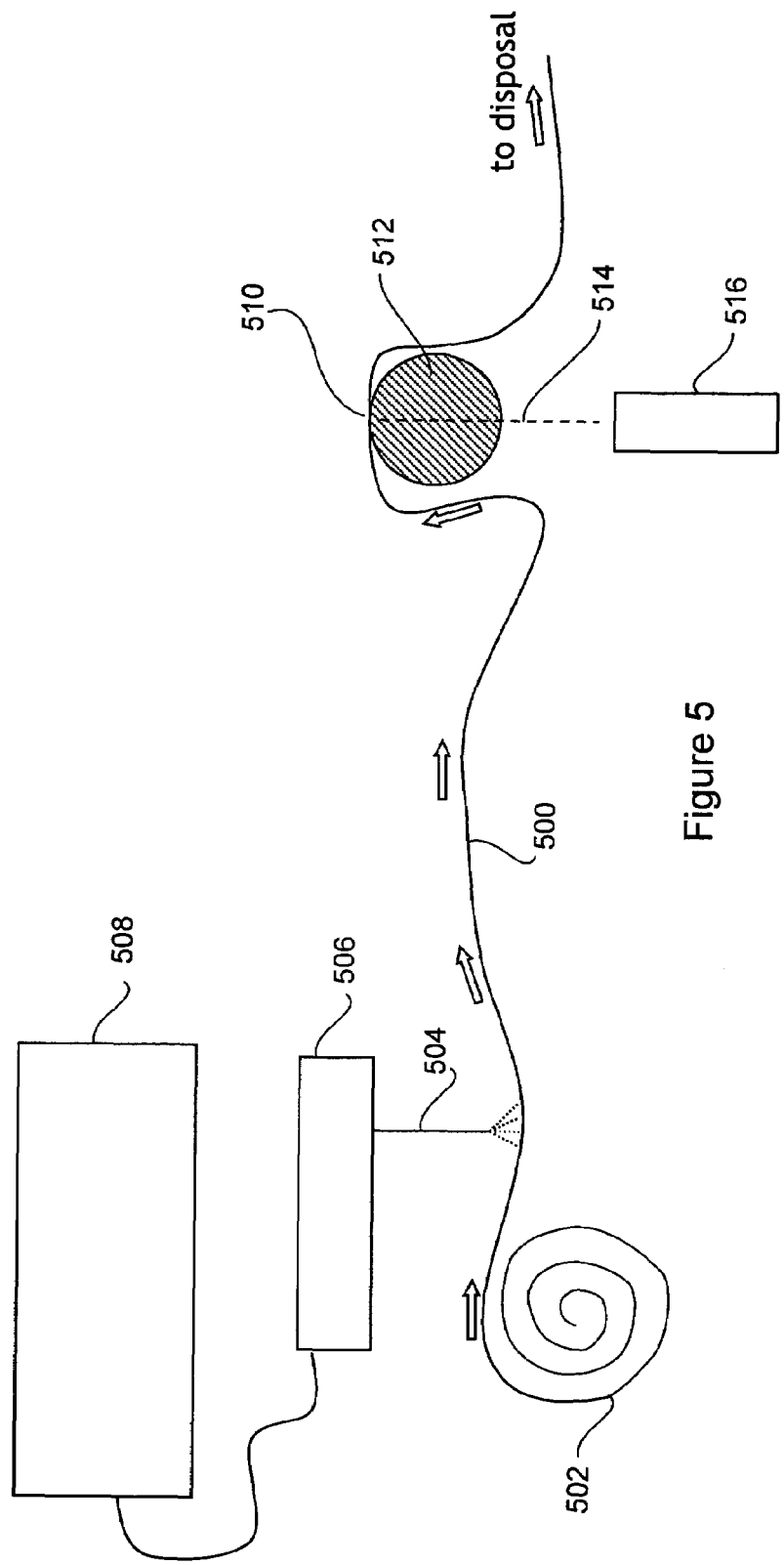
FIG. 5 is a simplified block diagram of an automated sampling system that utilizes a multiple sample holder, in accordance with an embodiment of the instant invention; and, FIG. 6 is a simplified block diagram of another automated sampling system that utilizes a multiple sample holder, in accordance with an embodiment of the instant invention and, FIG. 7 is a simplified flow diagram of a method of seperating ions according to an embodiment of the instant invention.

Referring now to FIG. 5, shown is a simplified block diagram of an automated sampling system that utilizes a multiple sample holder, in accordance with an embodiment of the instant invention. In FIG. 5, the multiple sample holder is provided in the form of a multiple sample holder strip 500, similar to the multiple sample holder shown at FIG. 4b. During use, the multiple sample holder strip 500 is held in a coil or similar reservoir 502. In operation this sample holder strip 500 is transported past the tip of a sample delivery capillary 504 that is part of a sample applicator 506. The control of this sample application, and the reservoirs of individual sample to be applied are housed in the autosampler 508. After application of the sample, the multiple sample holder strip 500 is translated using a not illustrated actuator to a MALDI ion forming region 510 that is adjacent a not illustrated ion inlet orifice of FAIMS 512. Further detail of the ion forming region 510 is shown at FIG. 1. Still referring to FIG. 5, after each sample is analyzed in region 510, the multiple sample holder strip 500 is stepwise translated using the actuator, to bring a next discrete target region of the multiple sample holder strip 500 to the ion forming region 510. One or more pulses of laser beam 514 generated by laser source 516 are directed to the sample, and ions are formed by a MALDI and/or gas phase ionization process. The ions thereby formed are analyzed in FAIMS 512, and are optionally further analyzed by other FAIMS or detection/analyzers, such as for instance mass spectrometry. In the embodiment shown in FIG. 5 the laser beam 514 passes through at least one of the electrodes of FAIMS 512, so that the multiple sample holder strip 500 does not have to be transparent to the laser beam. Optionally, the laser source 516 is relocated in such a way that the laser beam 514 strikes the multiple sample holder strip 500 from a side opposite the deposited sample, as is shown in FIG. 2.

Figure 6:
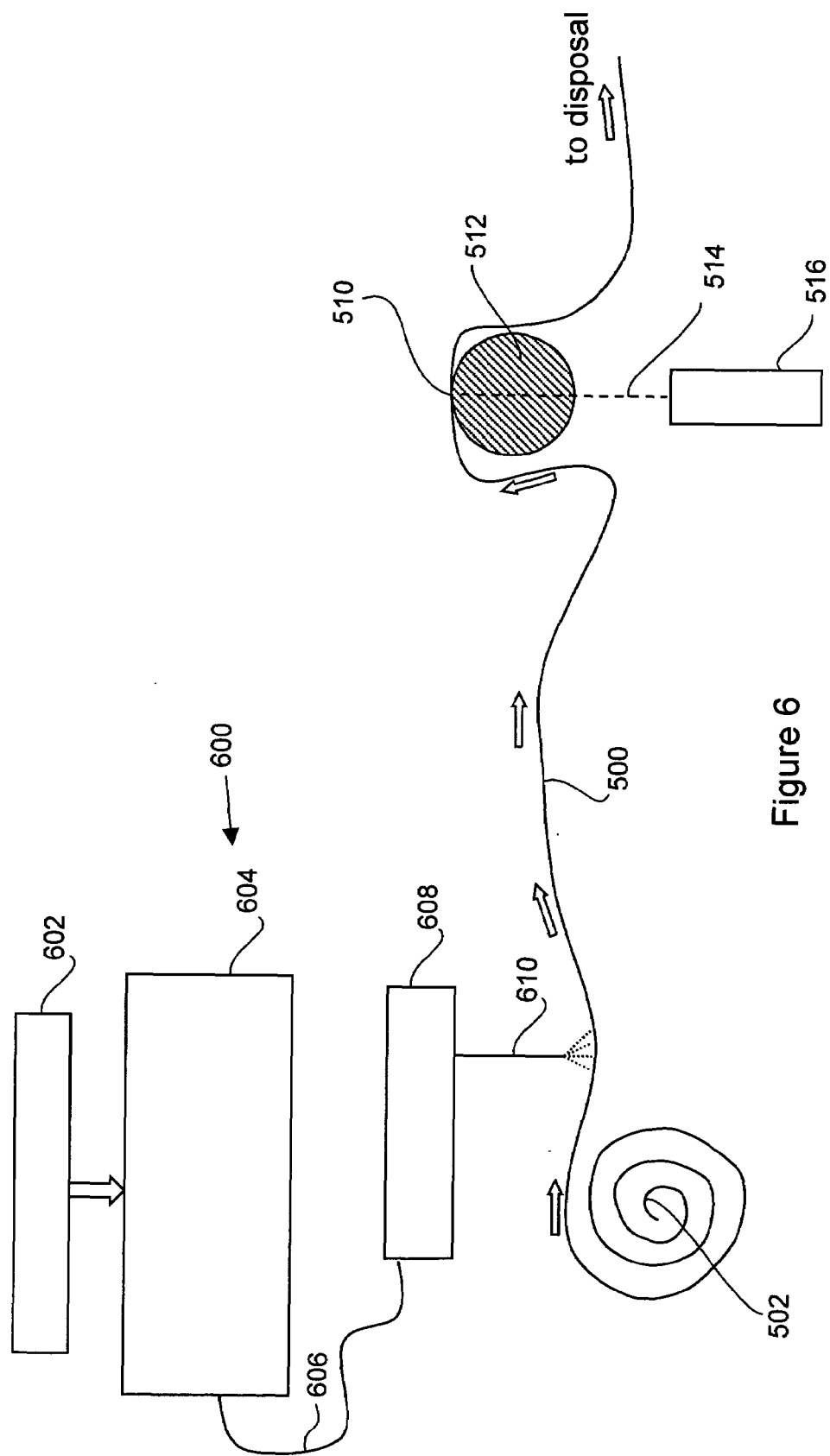

Referring now to FIG. 6, shown is a simplified block diagram of another automated sampling system that utilizes a multiple sample holder, in accordance with an embodiment of the instant invention. Elements labeled with the same numerals have the same function as those illustrated in FIG. 5. However, unlike FIG. 5 the sample is not provided by an autosampler which is designed to apply discrete types of samples individually on the multiple sample holder strip 500. Instead, the sample is provided from a condensed phase separation system 600. Injector unit 602 injects a portion of a sample into separation system 604 and the components of the sample are separated within the separation system 604. The effluent from such a separation typically contains the components and/or subsets of the components delivered, sequentially in time, out of the outlet capillary 606 of the separation system 604. The flowing liquid effluent is then directed through a sampler system 608 that has provision for applying portions of the liquid via a capillary applicator 610 to the multiple sample holder strip 500. The multiple sample holder strip 500 optionally includes individual discrete target regions, such as the discrete target regions 404 shown at FIG. 4b. Preferably for this application, the multiple sample holder strip 500 supports application of a continuous and non-interrupted flow of sample to the surface of multiple sample holder strip 500. A not illustrated actuator is used to continuously pass the multiple sample holder strip 500 through the MALDI laser beam 514, for continuous recording of the components eluted from the condensed phase separations system 600. Optionally, computer programming of the actuator supports automatically slowing down the transport of multiple sample holder strip 500 when few (or no) compounds of interest are being eluted from the condensed phase separation system 600, and increasing the transport speed during delivery of mixtures of interest. Further optionally, a portion of a distance that the multiple sample holder strip 500 travels between the capillary applicator 610 and the MALDI ionization region 510, includes a sample dryer for drying or otherwise modifying the samples deposited on the multiple sample holder strip 500.

Figure 7:
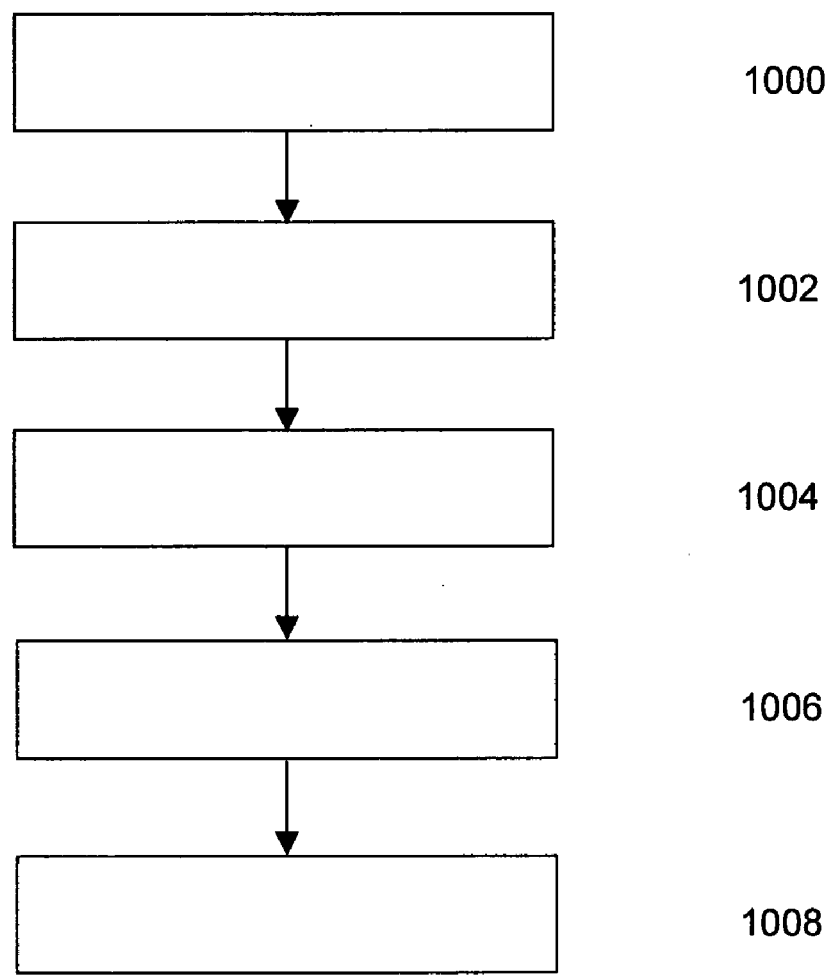

Referring now to FIG. 7, shown is a simplified flow diagram of a method of separating ions according to an embodiment of the instant invention. At step 1000, a sample material is applied to a sample holder, such that sample material is disposed about first and second points along the sample holder. In particular, a distance between the first and second points is greater than a maximum dimension of an ion inlet orifice of a FAIMS analyzer. At step 1002, the first point is aligned with the ion inlet orifice of the FAIMS analyzer. At step 1004 the sample material disposed about the first point is irradiated with laser light of a predetermined wavelength. At step 1006, the sample holder is moved relative to the ion inlet so as to align the second point with the ion inlet orifice of the FAIMS analyzer. At step 1008, the sample material disposed about the second point is irradiated with laser light of a predetermined wavelength.

Numerous other embodiments may be envisaged without departing from the spirit and scope of the invention.

What is claimed is:

1. An apparatus for separating ions, comprising:
    a FAIMS analyzer comprising a first electrode and a second electrode that is spaced apart from the first electrode, a space between the first electrode and the second electrode defining an analyzer region;
    an ion inlet orifice defined within a portion of the first electrode, for providing fluid communication between the analyzer region and a region that is external to the analyzer region; and,
    a laser-based ionization source comprising a laser light source and a multiple sample holder, the multiple sample holder disposed within the region that is external to the analyzer region for supporting each of a plurality of discrete sample portions, during different non-overlapping periods of time, in an aligned relationship with the ion inlet orifice, wherein the laser light source is synchronized to irradiate, with light of a predetermined wavelength, each of the plurality of discrete sample portions when in the aligned relationship with the ion inlet orifice.

2. An apparatus according to claim 1, wherein the multiple sample holder comprises a support material for supporting a plurality of discrete target regions, each discrete target region of the plurality for supporting one discrete sample portion.

3. An apparatus according to claim 2, wherein the multiple sample holder comprises one row of discrete target regions.

4. An apparatus according to claim 2, wherein the multiple sample holder comprises a two-dimensional array of discrete target regions.

5. An apparatus according to claim 2, wherein at least some of the discrete target regions comprise a mesh material.

6. An apparatus according to claim 5, wherein the mesh material is an electrically conductive material.

7. An apparatus according to claim 2, wherein at least some of the discrete target regions are at least partly porous for supporting a flow of a gas therethrough.

8. An apparatus according to claim 2, wherein each discrete target portion has a front surface for being disposed in a facing relationship with the ion inlet orifice, and wherein during use the one discrete sample portion is supported on the front surface.

9. An apparatus according to claim 8, wherein each discrete target region is at least partially transmissive to the light of a predetermined wavelength and wherein the laser light source is disposed for irradiating a back surface of each discrete target region.

10. An apparatus according to claim 8, comprising a laser orifice defined within the second electrode, wherein the laser light source is disposed for launching the light of a predetermined wavelength along an optical path including the laser orifice and the ion inlet orifice, for irradiating the front surface of each discrete target region.

11. An apparatus according to claim 10, wherein the optical path is a folded optical path including a reflective surface.

12. An apparatus for separating ions, comprising:
a FAIMS analyzer comprising a first electrode and a second electrode that is spaced apart from the first electrode, a space between the first electrode and the second electrode defining an analyzer region;
an ion inlet orifice comprising a finite-sized opening that is defined within a portion of the first electrode, the ion inlet orifice for providing fluid communication between the analyzer region and a region that is external to the analyzer region; and,
a laser-based ionization source for producing ions from a sample material, the laser-based ionization source comprising:
a sample holder disposed within the region that is external to the analyzer region, the sample holder having at least a target region for supporting a sample material, the at least a target region including a first portion and a second portion, the first portion and the second portion combined having a total surface area that is larger than the finite-sized opening of the ion inlet orifice;
an actuator for moving the sample holder relative to the ion inlet orifice, so as to align the first portion of the at least a target region with the ion inlet orifice during a first period of time and to align the second portion of the at least a target region with the ion inlet orifice during a second period of time; and,
a laser light source disposed to irradiate, with light of a predetermined wavelength, the first portion of the at least a target region during the first period of time and the second portion of the at least a target region during the second period of time.

13. An apparatus according to claim 12, wherein the sample holder is a multiple sample holder and wherein the first portion of the at least a target region is a first discrete target region and the second portion of the at least a target region is a second discrete target region.

14. An apparatus according to claim 13, wherein the multiple sample holder comprises one row of discrete target regions including the first discrete target region and the second discrete target region.

15. An apparatus according to claim 13, wherein at least one of the first discrete target region and the second discrete target region is at least partly porous for supporting a flow of a gas therethrough.

16. An apparatus according to claim 12, wherein the sample holder comprises a plurality of discrete target regions, each discrete target region for supporting a sample material and being spaced-apart from every other discrete target region of the plurality of discrete target regions.

17. An apparatus according to claim 16, wherein each discrete target region has a front surface for being disposed in a facing relationship with the ion inlet orifice, and wherein during use the sample material is supported on the front surface.

18. An apparatus according to claim 17, wherein each discrete target region is at least partially transmissive to the light of a predetermined wavelength and wherein the laser light source is disposed for irradiating a back surface of each discrete target region.

19. An apparatus according to claim 17, comprising a laser orifice defined within the second electrode, wherein the laser light source is disposed for launching the light of a predetermined wavelength along an optical path including the laser orifice and the ion inlet orifice, for irradiating the front surface of each discrete target region.

20. An apparatus according to claim 16, wherein at least some of the discrete target regions are at least partly porous for supporting a flow of a gas therethrough.

21. A method of separating ions, comprising:
providing a FAIMS analyzer region including an ion inlet orifice for providing ions thereto;
providing a sample holder along a side of the ion inlet orifice that is opposite the FAIMS analyzer region;
applying a sample material to the sample holder such that sample material is disposed about first and second points along the sample holder, a distance between the first and second points being greater than a maximum dimension of the ion inlet orifice;
aligning the first point with the ion inlet orifice;
irradiating the sample material disposed about the first point with laser light of a predetermined wavelength;
moving the sample holder relative to the ion inlet so as to align the second point with the ion inlet orifice; and,
irradiating the sample material disposed about the second point with laser light of a predetermined wavelength.

22. A method according to claim 21, wherein irradiating the sample material comprises irradiating a side of the sample holder on which the sample material is disposed.

23. A method according to claim 21, wherein irradiating the sample material comprises irradiating a side of the sample holder opposite a side on which the sample material is disposed.

24. A method according to claim 21, wherein applying a sample material to the sample holder comprises applying a first portion of an effluent from a condensed phase separation system about the first point and applying a second portion of an effluent from a condensed phase separation system about the second point.

25. A method according to claim 24, wherein the effluent from a condensed phase separation system is applied continuously between the first point and the second point.

* * * * *